United States Patent
Watson et al.

[11] Patent Number: 6,072,309
[45] Date of Patent: Jun. 6, 2000

[54] PAPER STOCK ZETA POTENTIAL MEASUREMENT AND CONTROL

[75] Inventors: John David Watson, Etobicoke, Canada; Hung-Tzaw Hu, Saratoga, Calif.; Claud Hagart-Alexander, Vancouver, Canada; Lee Chase, Los Gatos; John D. Goss, San Jose, both of Calif.

[73] Assignee: Honeywell-Measurex Corporation, Inc., Cupertino, Calif.

[21] Appl. No.: 09/065,408

[22] Filed: Apr. 23, 1998

Related U.S. Application Data

[63] Continuation-in-part of application No. 08/766,864, Dec. 13, 1996, Pat. No. 5,891,306.

[51] Int. Cl.[7] ................................................. G01N 27/00
[52] U.S. Cl. ...................... 324/71.1; 324/664; 324/665; 324/452
[58] Field of Search ..................... 162/363, 198, 162/DIG. 11; 324/664, 665, 694, 695, 71.1, 688, 452

[56] References Cited

U.S. PATENT DOCUMENTS

| | | |
|---|---|---|
| 3,260,642 | 7/1966 | Canter . |
| 3,593,128 | 7/1971 | Perry . |
| 3,630,836 | 12/1971 | Bietry et al. . |
| 3,636,327 | 1/1972 | Troutman . |
| 3,646,434 | 2/1972 | Norwich ................................. 324/61 R |
| 3,654,075 | 4/1972 | Keyes et al. . |
| 3,713,966 | 1/1973 | Lippke . |
| 3,723,712 | 3/1973 | Komline, Sr. et al. . |
| 3,723,865 | 3/1973 | Batey et al. . |
| 3,795,984 | 3/1974 | Meyer . |
| 3,811,087 | 5/1974 | Schmelzer . |
| 3,864,626 | 2/1975 | MacLean et al. . |
| 3,909,380 | 9/1975 | Day et al. . |
| 3,986,110 | 10/1976 | Overall et al. . |
| 4,135,151 | 1/1979 | Rogers et al. . |
| 4,259,632 | 3/1981 | Ahtiainen . |
| 4,314,878 | 2/1982 | Lee . |
| 4,329,201 | 5/1982 | Bolton . |
| 4,369,080 | 1/1983 | Johnson . |
| 4,398,996 | 8/1983 | Bolton et al. . |
| 4,468,611 | 8/1984 | Tward . |
| 4,474,643 | 10/1984 | Lindblad . |
| 4,514,812 | 4/1985 | Miller et al. . |
| 4,535,285 | 8/1985 | Evans et al. ........................... 324/71.1 |

(List continued on next page.)

FOREIGN PATENT DOCUMENTS 0276106  7/1988  European Pat. Off. .

OTHER PUBLICATIONS

Smook, G.A., Handbook for Pulp & Paper Technologists, 2d. ed., (Angus Wilde Publications), pp. 228–229.

*Primary Examiner*—Josie Ballato
*Assistant Examiner*—Vincent Q. Nguyen
*Attorney, Agent, or Firm*—Burns, Doane, Swecker & Mathis LLP

[57] ABSTRACT

System and method for producing paper that employ an apparatus for measuring electrical characteristics of a fibrous composition. The apparatus comprises a plurality of conductivity (or resistance) detectors each comprising a sensor that is sensitive to the conductivity (or resistance) and the proximity of the material (e.g., fibrous composition) to the sensor. Measurements from the apparatus relate to the zeta potential of the fibrous materials in the composition. The zeta potential profiles corresponding optimized configurations of the sheetmaking process can be employed to monitor and control the process.

11 Claims, 6 Drawing Sheets

U.S. PATENT DOCUMENTS

| | | |
|---|---|---|
| 4,580,233 | 4/1986 | Parker et al. . |
| 4,588,943 | 5/1986 | Hirth . |
| 4,613,406 | 9/1986 | Gess . |
| 4,648,715 | 3/1987 | Ford, Jr. et al. . |
| 4,680,089 | 7/1987 | Aral et al. . |
| 4,692,616 | 9/1987 | Hegland et al. . |
| 4,707,779 | 11/1987 | Hu . |
| 4,748,400 | 5/1988 | Typpo . |
| 4,786,529 | 11/1988 | Boissevain . |
| 4,791,353 | 12/1988 | Typpo . |
| 4,817,021 | 3/1989 | Sowerby et al. . |
| 4,827,121 | 5/1989 | Vidrine, Jr. et al. . |
| 4,840,706 | 6/1989 | Campbell . |
| 4,845,421 | 7/1989 | Howarth et al. ............ 324/61 R |
| 4,903,528 | 2/1990 | Balakrishnan . |
| 4,909,070 | 3/1990 | Smith . |
| 4,921,574 | 5/1990 | Hu . |
| 4,924,172 | 5/1990 | Holmgren . |
| 4,947,684 | 8/1990 | Balakrishnan . |
| 4,957,770 | 9/1990 | Howarth . |
| 4,980,846 | 12/1990 | Chapman . |
| 4,986,410 | 1/1991 | Shields . |
| 4,990,261 | 2/1991 | Ho . |
| 4,994,145 | 2/1991 | Seymour . |
| 5,013,403 | 5/1991 | Chase . |
| 5,020,469 | 6/1991 | Boissevain et al. . |
| 5,021,740 | 6/1991 | Sarr et al. . |
| 5,022,966 | 6/1991 | Hu . |
| 5,045,798 | 9/1991 | Hendrick . |
| 5,052,223 | 10/1991 | Regnault et al. . |
| 5,067,345 | 11/1991 | Mougne . |
| 5,093,795 | 3/1992 | Lewis . |
| 5,122,754 | 6/1992 | Gotaas . |
| 5,124,552 | 6/1992 | Anderson . |
| 5,132,631 | 7/1992 | Klopfenstein et al. . |
| 5,134,380 | 7/1992 | Jonas . |
| 5,170,128 | 12/1992 | Masurat et al. . |
| 5,170,670 | 12/1992 | Fasching et al. . |
| 5,177,445 | 1/1993 | Cross . |
| 5,198,777 | 3/1993 | Masuda et al. . |
| 5,206,599 | 4/1993 | Mayer . |
| 5,208,544 | 5/1993 | McBrearty et al. . |
| 5,225,785 | 7/1993 | Mayer et al. . |
| 5,241,280 | 8/1993 | Aidun et al. . |
| 5,244,550 | 9/1993 | Inoue . |
| 5,247,261 | 9/1993 | Gershenfeld . |
| 5,262,955 | 11/1993 | Lewis . |
| 5,270,664 | 12/1993 | McMurtry et al. . |
| 5,280,250 | 1/1994 | Jayaweera et al. ............ 324/452 |
| 5,340,442 | 8/1994 | Gess et al. . |
| 5,400,247 | 3/1995 | He . |
| 5,450,015 | 9/1995 | Mastico et al. ............ 324/665 |
| 5,492,601 | 2/1996 | Ostermayer et al. . |
| 5,493,910 | 2/1996 | Hall et al. . |
| 5,539,634 | 7/1996 | He . |
| 5,561,599 | 10/1996 | Lu . |
| 5,563,809 | 10/1996 | Williams et al. . |
| 5,636,126 | 6/1997 | Heaven et al. . |
| 5,658,432 | 8/1997 | Heaven et al. . |

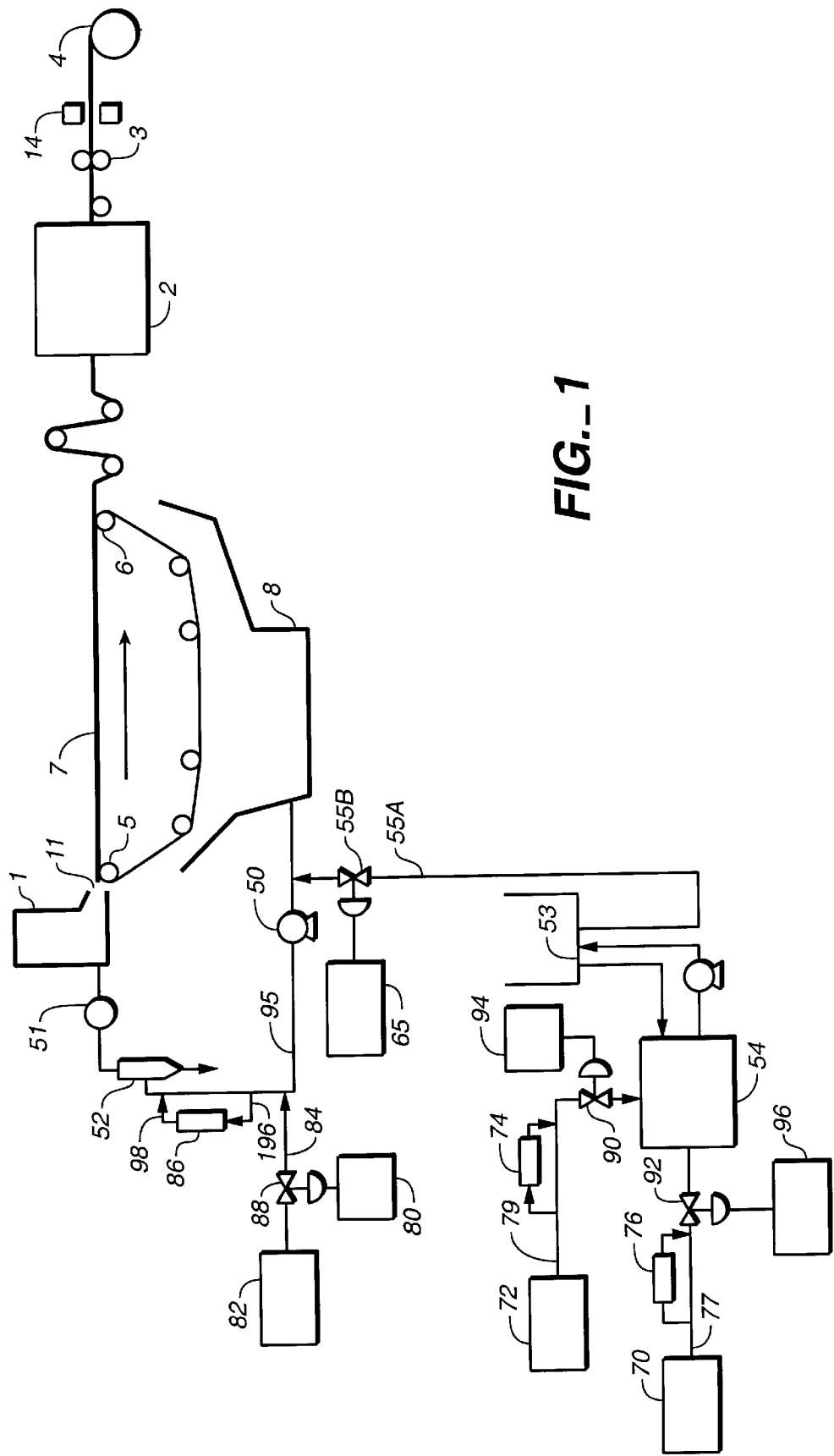
FIG._1

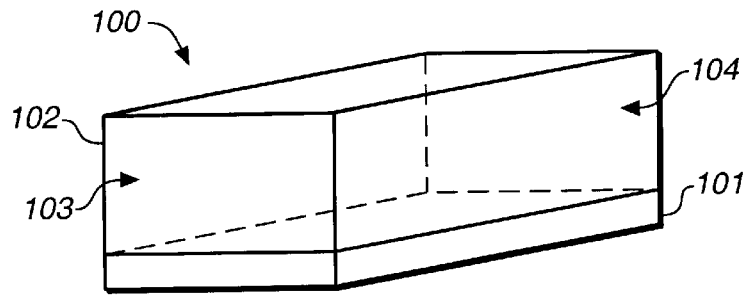
FIG._2A
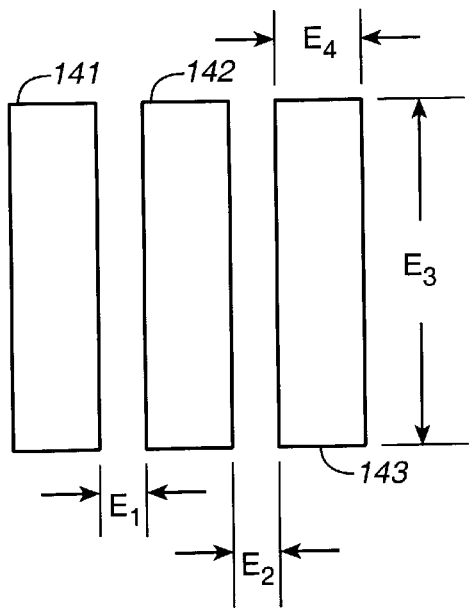
FIG._2C
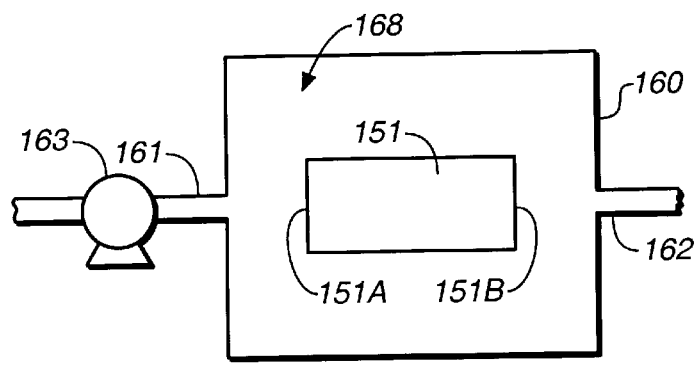
FIG._2E

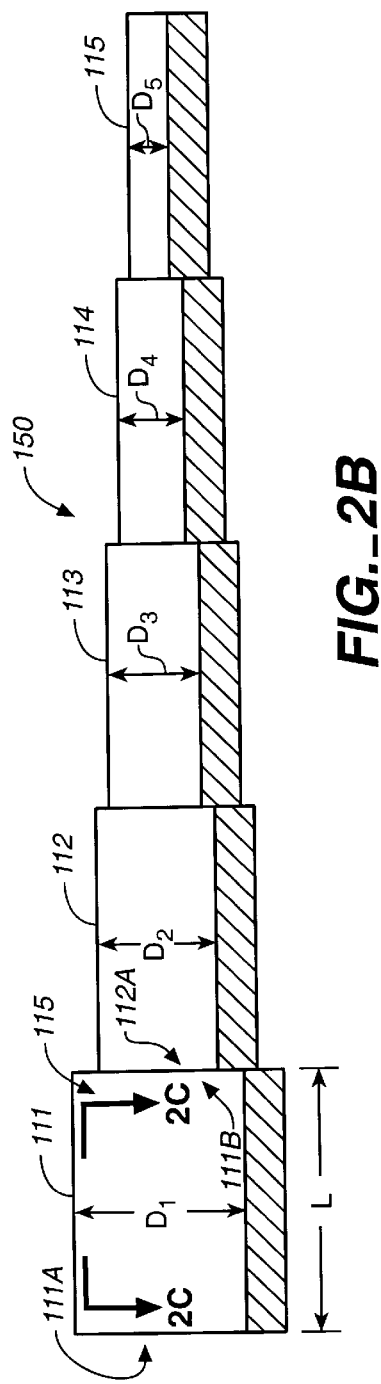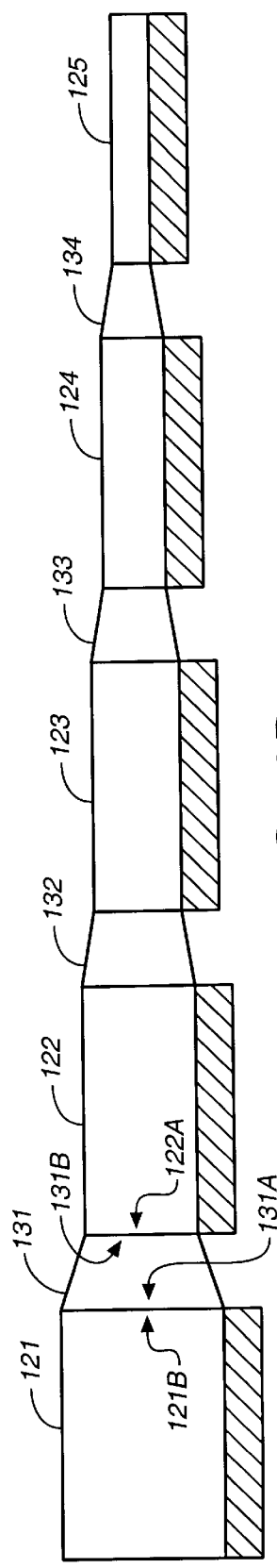
FIG._2B
FIG._2D

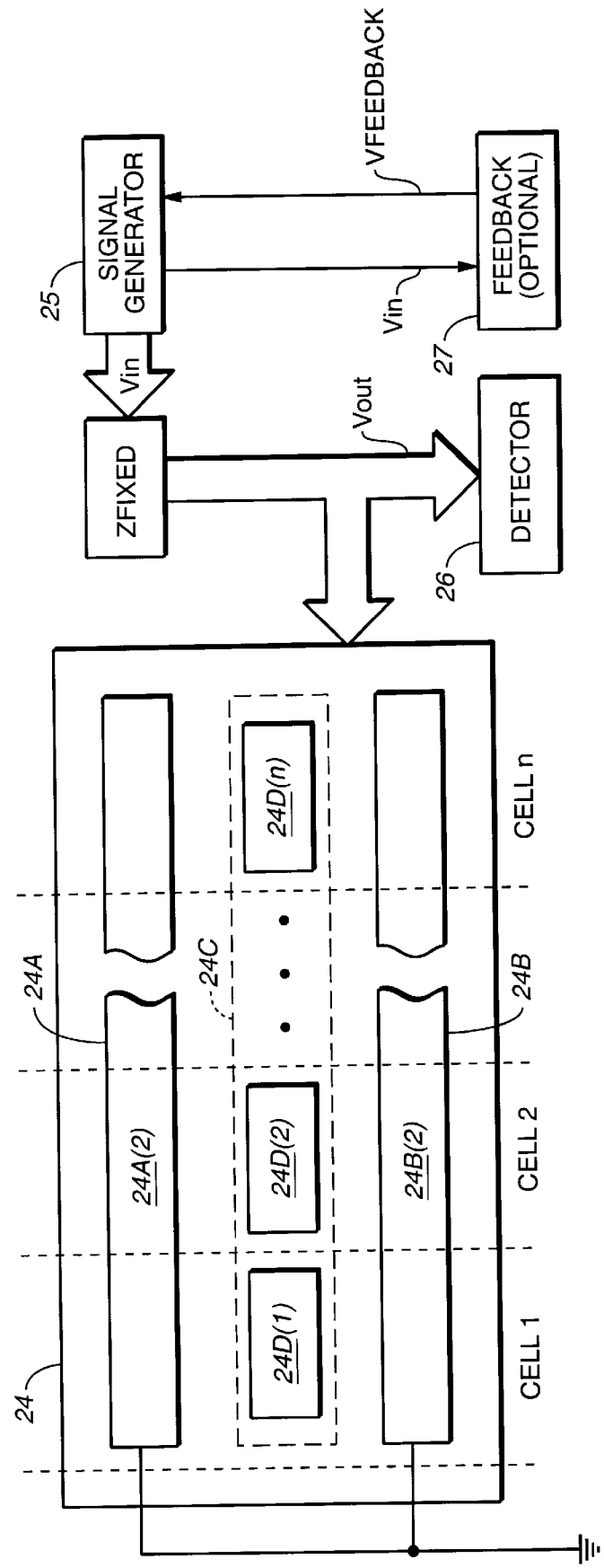
FIG._3

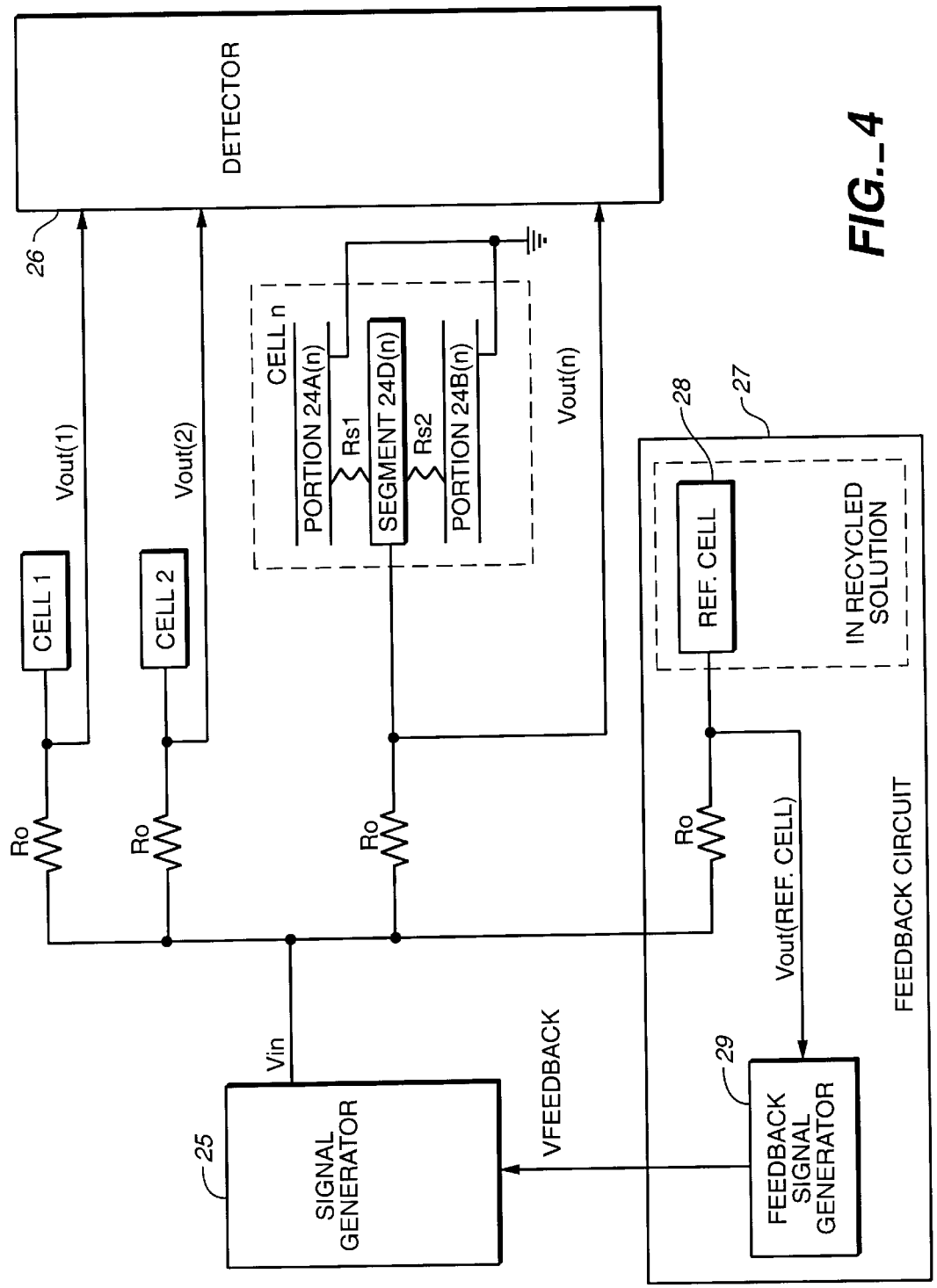
FIG._4

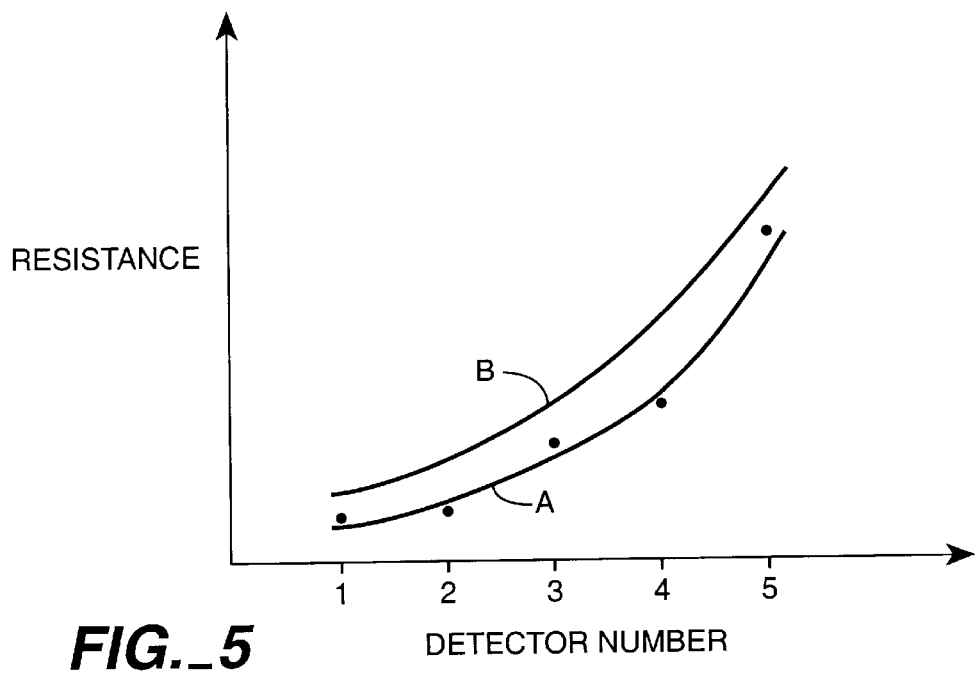
FIG._5
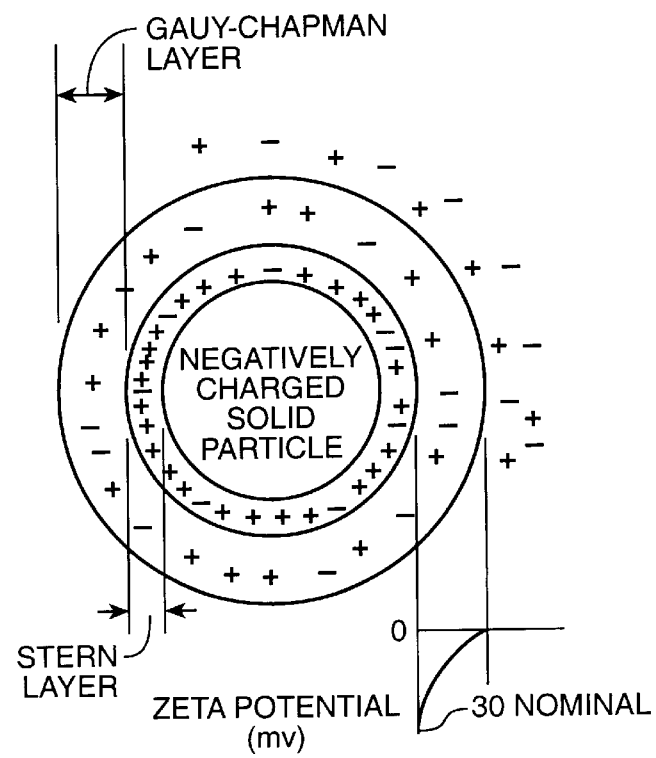
FIG._6

PAPER STOCK ZETA POTENTIAL MEASUREMENT AND CONTROL

This is a continuation-in-part of U.S. patent application Ser. No. 08/766,864, filed on Dec. 13, 1996, now U.S. Pat. No. 5,891,306.

FIELD OF THE INVENTION

The present invention generally relates to controlling continuous sheetmaking and, more specifically, to measuring electrical characteristics of a fibrous dispersion and to controlling the flow rate of chemical additives into the furnish that enters the headbox.

BACKGROUND OF THE INVENTION

In the art of making paper with modern high-speed machines, sheet properties must be continually monitored and controlled to assure sheet quality and to minimize the amount of finished product that is rejected when there is an upset in the manufacturing process. The sheet variables that are most often measured include basis weight, moisture content, and caliper (i.e., thickness) of the sheets at various stages in the manufacturing process. These process variables are typically controlled by, for example, adjusting the feedstock supply rate at the beginning of the process, regulating the amount of steam applied to the paper near the middle of the process, or varying the nip pressure between calendaring rollers at the end of the process. Papermaking devices well known in the art are described, for example, in "Handbook for Pulp & Paper Technologists" 2nd ed., G. A. Smook, 1992, Angus Wilde Publications, Inc., and "Pulp and Paper Manufacture" Vol. III (Papermaking and Paperboard Making), R. MacDonald, ed. 1970, McGraw Hill. Sheetmaking systems are further described, for example, in U.S. Pat. Nos. 5,539,634, 5,022,966 4,982,334, 4,786,817, and 4,767,935.

In the manufacture of paper on continuous papermaking machines, a web of paper is formed from an aqueous suspension of fibers (wet stock) on a traveling mesh papermaking fabric and water drains by gravity and vacuum suction through the fabric. The web is then transferred to the pressing section where more water is removed by dry felt and pressure. The web next enters the dryer section where steam heated dryers and hot air completes the drying process. The paper machine is essentially a de-watering system. In the sheetmaking art, the term machine direction (MD) refers to the direction that the sheet material travels during the manufacturing process, while the term cross direction (CD) refers to the direction across the width of the sheet which is perpendicular to the machine direction.

A wide range of chemicals is utilized in the papermaking stock furnish to impart or enhance specific sheet properties or to serve other necessary purposes Such additives as alum, sizing agents, mineral fillers, starches and dyes are commonly used. Chemicals for control purposes such as drainage aids, defoamers, retention aids, pitch dispersants, slimicides, and corrosion inhibitors are added as required. The order of addition must be taken into account to prevent interaction at the wrong time and enhance retention in the paper sheet.

Wet end chemistry deals with all the interactions between furnish materials and the chemical/physical processes occurring at the wet end of the papermaking machine. The major interactions at the molecular and colloidal level are surface charge, flocculation, coagulation, hydrolysis, time-dependent chemical reactions and microbiological activity. These interactions are fundamental to the papermaking process. For example, to achieve effective retention, drainage, sheet formation, and sheet properties, it is necessary that the filler particles, fiber fines, size and starch be flocculated and/or adsorbed onto the large fibers with minimal flocculation between the large fibers themselves.

There are three major groups involved in wet-end chemistry: solids, colloids and solubles. Most attention is focused on the solids and their retention. In order to maximize retention, it is important to cause the fines and fillers to approach each other and form bonds or aggregates which are stable to the shear forces encountered in the paper machine headbox and approach system. In modern papermaking, this is usually accomplished by using synthetic polymers.

Control of wet-end chemistry is vital to ensure that a uniform paper product is manufactured. If the system is allowed to get out of balance (e.g., by over-use of cationic polymers), the fibers themselves will become flocculated and sheet formation will suffer. Also, functional additives (e.g., sizes, wet-strength agents) are often added at the wet end; if the chemistry is not under control, the functionality may not be adequately imparted and the product will be off-quality.

As is apparent, there is a wide range of phenomena which can influence the fundamental interactions at the molecular and colloidal. One of these factors is the electrokinetics. In this regard, the term, zeta potential, applies to the electrical charges existing in fine dispersions. Referring to FIG. 6, a solid particle (e.g., fiber, starch, mineral) suspended in a papermaking stock is surrounded by a dense layer of ions having a specific electrical charge. This layer is surrounded by another layer, more diffuse than the first, that has an electrical charge of its own. The bulk of the suspended liquid also has its own electrical charge. The difference in electrical charge between the dense layer of ions surrounding the particle and the bulk of the suspended liquid is the zeta potential, usually measured in millivolts. The zeta potential, $\zeta$, and is defined by the equation:

$$\zeta = \frac{4\pi\delta q}{D}$$

where q is the charge on the particle, $\delta$, is the thickness of the zone of influence of the charge on the particle, and D is the dielectric constant of the liquid. Measurements of zeta potential can give an indication of the effectiveness of added electrolytes in lowering the energy barrier between colloids, and thus can serve to guide the selection of optimum conditions for coagulation.

The best retention of fine particles and colloids in the papermaking system normally occurs when the zeta potential is near zero. Pulp fibers, filler and size particles usually carry a negative charge, but the zeta potential can be controlled by absorbing positive ions from solution. Polyvalent cations such as aluminum and ferric are most effective.

Papermakers alum, $Al_2(SO_4)_3$, is still a commonly used agent for wet end chemistry because it effectively neutralizes the negatively-charged fiber and pigment particles to zero zeta potential. At the proper pH, it also hydrolyzes to form an ionic polymer that has a significant flocculating effect by bridging from particle to particle and thereby forming large ionically-attracted flocs.

SUMMARY OF THE INVENTION

The present invention is based in part on the development of an apparatus for measuring electrical characteristics of an aqueous fibrous composition. The apparatus comprises a plurality of detectors each comprising a sensor that is sensitive to at least the properties of materials: the conductivity (or resistance), the dielectric constant, and the proximity of the material (e.g., fibrous composition) to the sensor. The apparatus provides an indirect method of measuring the zeta potential of the fiber particles in the aqueous fibrous composition.

In one aspect, the invention is directed to an apparatus for measuring an electrical characteristic of an aqueous fibrous composition comprising fibers dispersed in an aqueous phase, that includes at least three detectors, designated $d_1$, $d_2$, $d_3$, and so on, that are sensitive to properties of the fibrous composition and which are positioned in tandem wherein each detector includes:

(a) an impedance element; and (b) a sensor including a first electrode and a second electrode which is spaced-apart and adjacent to said first electrode, a portion of said aqueous fibrous composition being between and in close proximity to said first and said second electrodes, said sensor coupled in series with said impedance element between an input signal and a reference potential, wherein fluctuations in at least one of the properties cause changes in voltage across said sensor, wherein each detector comprises a housing having an inlet and outlet and defining a channel having through which said aqueous fibrous composition travels, wherein the outlet of a first conductivity detector $d_1$ is in communication with the inlet of a second conductivity detector $d_2$, the outlet of $d_2$ is in communication with the inlet of a third conductivity detector $d_3$, and so on, and wherein the channels of said at least three detectors have different configurations.

The method for optimizing the operation of a papermaking machine to produce a specific paper grade comprises a three-step procedure. The first step comprises tuning process parameters of the papermaking machine to obtain an optimized configuration which produces acceptable quality paper as determined by direct measurement. A zeta potential measurement profile corresponding to this optimized configuration is then taken with the inventive apparatus and recorded.

This optimal profile may then be fitted to various parameterized functions (such as an exponential) using standard curve fitting techniques. This curve fitting procedure has the effect of smoothing out the effects of noise on the profile, and interpolating between measured points.

During subsequent production runs of the papermaking machine, the objective is to reproduce the previously determined optimal profile. If the measured zeta potential is either above or below the optimal profile, the process parameters, such as the chemical additives flow rate, are adjusted as necessary to bring that measurement closer toward the optimal profile.

BRIEF DESCRIPTION OF THE DRAWINGS

FIG. 1 shows a sheetmaking system implementing the technique of the present invention;

FIGS. 2A, 2B, 2C, 2D and 2E show embodiments of the zeta potential apparatus;

FIG. 3 shows a block diagram of a measurement apparatus including a sensor array;

FIG. 4 shows an electrical representation of the block diagram shown in FIG. 3;

FIG. 5 is a graph of stock resistance versus cell number in a zeta potential apparatus detector number; and FIG. 6 is a pictorial representation of zeta potential.

DETAILED DESCRIPTION OF PREFERRED EMBODIMENTS

The present invention relates to sheetmaking systems that include an apparatus that measures an electrical characteristic of the wet stock from which the sheet is fabricated. Although the invention will be described as part of a fourdrinier papermaking machine, it is understood that the invention is applicable to other papermaking machines including, for example, twin wire and multiple headbox machines and to paper board formers such as cylinder machines or Kobayshi Formers. Some conventional elements of a papermaking machine are omitted in the following disclosure in order not to obscure the description of the elements of the present invention.

FIG. 1 shows a system for producing continuous sheet material that comprises processing stages including headbox 1, web or wire 7, dryer 2, calendaring stack 3, and reel 4. Actuators (not shown) in headbox 1 discharge wet stock (e.g., pulp slurry) through a plurality of slices 11 onto supporting wire 7 which rotates between rollers 5 and 6. Foils and vacuum boxes (not shown) remove water, commonly known as "white water", from the wet stock on the wire into wire pit 8 for recycle. A scanning sensor 14 continuously traverses the finished sheet (e.g., paper) and measures properties of the finished sheet. Multiple stationary sensors could also be used. Scanning sensors are known in the art and are described, for example, in U.S. Pat. Nos. 5,094,535, 4,879,471, 5,315,124, and 5,432,353, which are incorporated herein. The finished sheet is then collected on reel 4. As used herein, the "wet end" portion of the system comprises the headbox, the web, and those sections just before the dryer, and the "dry end" comprises the sections that are downstream from the wire. The term "water weight" refers to the mass or weight of water per unit area of the wet paper stock which is on the wire. The term "dry weight" or "dry stock weight" refers to the weight of a material (excluding any weight due to water) per unit area.

Typically, the papermaking furnish or raw material is metered, diluted, mixed with any necessary additives, and finally screened and cleaned as it is introduced into headbox 1 from fan pump 50. The stock or furnish entering the headbox typically contains about 0.5 to 5 (wt) % fibrous materials. Although stock from machine chest 54 should be reasonable free from impurities, papermaking machine approach systems usually utilize pressure screens 51 and centrifugal cleaners 52 to prevent contamination. The stock in machine chest 54 is often a blend comprising different wood fibers, e.g., combination of hardwood and softwood. As illustrated in this system, fiber source 70 supplies a fiber slurry through line 77 into machine chest 54. The flow through line 77 is regulated by valve 92 which is controlled by controller 96. Similarly a second fiber source 72 contributes a fiber slurry through line 79 into machine chest 54. The flow through line 77 is regulated by valve 90 which is controlled by controller 94. The fiber slurries from fiber sources 70 and 72 each typically contains about 2 (wt) % to 5 (wt) % fibrous materials. Finally, chemical additives are added to the stock from source 82 through line 84 which is regulated by valve 88 that is controlled by controller 80.

Chemical additives are added at different steps in the processes. Wet-end chemical and mineral additives include, for example, acids and bases, alum, sizing agents, dry-strength adhesives, wet-strength resins, fillers, coloring materials, retention aids, fiber flocculants, defoamers, drainage aids, optical brighteners, pitch control chemicals, slimicides, and specialty chemicals. Some of these chemicals, e.g., alum, can be employed to alter the zeta potential of fiber particles in the stock.

Fan pump 50 serves to mix the stock with the white water and deliver the blend to the headbox 1. To ensure a uniform dispersion to the headbox, the stock is fed from a constant head tank 53, commonly called the "stuff box," through a line 55A that is regulated by control valve 55B (also called the basis weight valve). Control valve 55B is controlled by a first controller 65 that is responsive to, for example, basis weight measurements performed by scanner sensor 14 at the dry end. The term "basis weight" refers to the total weight of the material per unit area. The system further includes one or more apparatuses, each herein referred to as a zeta potential apparatus or sensor, that indirectly measures the zeta potential of fiber particles in the stock. As an illustration, the system includes zeta potential apparatuses 74, 76, and 86. Devices 74 and 76 measure the aqueous fiber slurries from sources 70 and 72, respectively. Similarly, device 86 measures the aqueous stock just before it is introduced into the headbox. In each instance, a portion of the flow from the main line is diverted into the apparatus. For example, a portion of the wet stock from line 95 is diverted through line 196 into apparatus, and out through line 98 before returning to line 95.

Each zeta potential apparatus includes a series of detectors and each detector has a different cross sectional configuration, e.g., channel gap size, as shown in FIGS. 2A, 2B, 2C, and 2D. As used herein, the term "configuration" with respect to the cross section of the channel refers to either the geometry or dimension. Thus, for example, even if all the detectors have a square cross section, their configurations would be considered different if the lengths of the sides of the square cross sections are different.

FIG. 2A is a perspective view of one representative detector 100 which includes base 101 which supports housing 102 that defines a channel having an inlet 103 and an outlet 104. The housing and base are fabricated of non-electrically conductive material, e.g., plastic. The base encases electrodes of the detector and the electrodes are sensitive to three properties of materials: the conductivity or the resistance, the dielectric constant, and the proximity of the material to the electrodes. For aqueous fibrous compositions, the electrodes are particularly sensitive to the conductivity or resistance. Preferably, the cross-sectional area of the channel is constant along the entire length L of the detector from the inlet to the outlet so that the fluid velocity distribution for the fluid traveling through the channel will be uniform. The cross-section of the channel is preferably rectangular although other geometries, e.g., semi-circular cross-sections, can be employed.

FIG. 2B is a cross-sectional view of zeta potential apparatus 150 for detecting electrical characteristics that includes five detectors 111, 112, 113, 114, and 115 which are positioned in tandem. The zeta potential apparatus includes at least 3 detectors and preferably 4 to 6 detectors. Preferably each detector has a rectangular cross section. In this embodiment, detector 111 is contiguous with detector 112 so that fluid exiting the channel of detector 111 through outlet 111B enters the channel of detector 112 from inlet 112A and so on. The detectors are preferably constructed so that the cross-sectional area of a succeeding detector is less than that of the preceding one, or vice versa. Typically the succeeding detector will have a channel cross-section area that is about 20% to 40%, and preferably about 25% to 30% of the preceding channel cross-sectional area. In this fashion, the fluid sample average velocity increases as it travels through successive detectors in the apparatus of FIG. 2B.

The different height or gap sizes of the channels in the five detectors are designated $D_1$, $D_2$, $D_3$, $D_4$, and $D_5$, respectively. For the first detector, which typically has the largest channel, the height should be about 10 mm to 15 mm and preferably about 12 mm and the fifth detector should have a channel height of about 1 mm to 3 mm and preferably about 2 mm. In the preferred embodiment shown in FIG. 2B, each detector has a length L of about 20 mm, a width W of about 20 mm, and $D_1$, $D_2$, $D_3$, $D_4$, and $D_5$, are 10, 8, 6, 4, and 2 mm, respectively. As is apparent, although preferred, it is not essential that the gap sizes increase or decrease progressively. For example, in the case of a five detector apparatus wherein each detector has a different gap height, the detectors can be positioned in any sequence.

FIG. 2C, which is a plan view of detector 111, shows a three electrode arrangement including electrodes 141, 142, and 143, and the dimensions of the three electrodes in each of the five detectors are preferably the same. Electrodes 141 and 143 are grounded. Fluid flowing through the channels come into contact with these electrodes.

The embodiment illustrated in FIG. 2B may create "dead zones" in the channels where flow is interrupted. For example, in the area designated 115 near the outlet 111B of detector 111, fluid flow will be interrupted in this region due to the smaller gap size in detector 112. A method of ameliorating this adverse effect is to round the edges of the channels near the outlets of each detector.

FIG. 2D is a cross-sectional view of an embodiment of the zeta potential apparatus having a coupler which defines a conduit between adjacent detectors to provide a smooth transition from one detector to the next. In this embodiment, detectors 121, 122, 123, 124, and 125 are identical to detectors 111, 112, 113, 114, and 115, respectively, of the apparatus shown in FIG. 2B. Couplers 131, 132, 133, and 134 are positioned in between adjacent detectors. The couplers preferably all have the same overall shape but they will differ in size. Coupler 131, for example, comprises a funnel-like structure having an inlet 131A whose contour matches that of outlet 121B of detector 121 and having an outlet 131B whose contour matches that of inlet 122A of cell 122.

An aqueous, liquid mixture containing fiber particles when traveling through a channel of one of the detectors illustrated in FIG. 2B will disturb the electromagnetic fields created by electrodes 141, 142, and 142 as described herein. Consequently, for the zeta potential apparatus of FIG. 2B, when an aqueous, liquid mixture containing fiber particles travels successively through the five channels of the detectors, the electromagnetic fields in each detector will be disturbed. Furthermore, because the channel configuration changes from one detector to the next, the conductivity (or resistance) as measured by successive cells will differ. To enhance this phenomenon, it is preferred that the gap size be comparable relative to the distance between the adjacent electrodes. As shown in FIG. 2C, in a preferred embodiment, electrodes 141, 142, and 143 have substantially the same dimensions. Specifically, the width $E_4$ of each electrode is preferably from about 4.8 mm to 8 mm, the length of each electrode $E_3$ is preferably from about 19 mm to 32 mm, and the distances between the electrodes $E_1$ and $E_2$ are preferably the same and preferably range from about 2.4 mm to 4 mm. In a preferred embodiment, $E_1$ and $E_2$ are each about 0.125 in. (3.2 mm), $E_3$ is about 1.0 in. (25.4 mm) and $E_4$ is about 0.25 in. (6.4 mm). Relative to these dimensions of the electrodes, the gap height is preferably less than about 15 mm, and preferably ranges from 15 mm to 1 mm.

FIG. 2E shows a zeta potential apparatus 151, which can be equivalent to the one in FIG. 2B, that is encased in housing 160 having chamber 168 with inlet line 161 and outlet line 162. If necessary, pump 165 is used to introduce the stock or fiber slurry into the chamber at the requisite speed. Preferably, apparatus 151 is positioned in the chamber 168 so that stock flows into the apparatus through inlet 151A and exits through outlet 151B where the gap of outlet 151B is less than that of inlet 151A. It is understood that position of the apparatus can reversed so that the direction of flow through the apparatus is in the opposite direction.

It is preferred that the stock or fiber slurry exhibit turbulent flow characteristics as it travels through apparatus 151. This will reduce the likelihood that the fibers flocculate or otherwise bind together appreciablely as the stock travels through the channels of the detectors. Flocculation will change the surface character of the fiber particles and thereby alter the zeta potential of the fiber particles. It is expected that the fiber particles in the stock or fiber slurry as they are measured by the zeta potential apparatus under turbulent flow conditions will exhibit substantially the same physical characteristics, e.g., zeta potential, as the fiber particles in the stock or fiber slurry before being diverted for measurement. Preferably, the stock or fiber slurry flows through the channels at a rate of least at about 1.6 m/sec. to 2.6 m/sec. and more preferably at about 7 ft/sec. (2.1 m/sec.)

In operation of the zeta potential apparatus, the three electrodes in each detector will be exposed to the stock or slurry having substantially the same fiber particle size distribution and ionic strength. By measuring, for instance, the conductivity or resistance in a series of detectors, the zeta potential apparatus can differentiate between a change in ionic strength or particle size distribution and a change in ionic mobility. Specifically, a change in ionic strength or particle size distribution will change the conductivity measurement in each detector by a fixed amount whereas a change in ionic mobility will cause a differential change in the conductivity with changing gap size. The apparatus provides continuous zeta potential data which can be employed to control the rate of chemical and stock additive flow or other process parameters.

FIG. 5 is a graph of representative data from a zeta potential apparatus having five detectors as shown in FIG. 2B wherein the channels have gap sizes that decrease progressively from detectors 111 to 115. (Designated detectors 1 through 5 on the graph.) The direction of stock flow is from the detector with the largest gap size to the one with the smallest. As stock flows through each cell, the electrodes in each detector will measure the resistance of the stock. As shown in curve A of FIG. 5, the measured resistance increases non-linearly from detectors 1 to 5. It is believed that the shape of curve A (or profile) which is developed by standard curve fitting techniques is related to the zeta potential of the fiber particles in the stock.

Information from the zeta potential apparatus can be employed to control, for example, the flow rate of chemical additives (e.g., alum) into the stock. For example, one or more zeta potential profiles developed during operation of a papermaking machine can be employed to monitor the papermaking machine. The term "zeta potential profile" refers to a set of individual measurements as measured by the zeta potential apparatus. In the case where an apparatus includes 5 detectors, then one set of individual measurements has 5 resistance readings. Alternatively, the zeta potential profile can comprise a curve that is developed by standard curve fitting techniques from the five readings. A database of zeta potential profiles is created for different grades of paper that are made under different operating conditions including different ambient conditions (e.g., temperature and humidity). For instance, when the machine of FIG. 1 is operating and making a specific grade of paper that has the desired physically properties as determined by laboratory analysis and/or measurement by the scanning sensor, measurements are then taken with the zeta potential apparatus. The measurements will be employed to create a base or optimal zeta potential profile for that specific grade of paper and under the specific conditions. A database containing base zeta potential profiles (or base profiles) for different grades of paper manufactured under various operating conditions is developed. It should be noted that besides developing and maintaining a database of the base zeta potential profiles, operating parameters relating to the chemical additives (e.g., their rates of addition), the stock jet speed to wire speed ratio for each profile will also be recorded. This ratio will be close to but not equal to 1. In this fashion, when the base profile from the database is employed to operate the papermaking machine, initially the machine will begin operation at the recorded operating parameters. Thereafter, chemical addition can be manipulated in order to reproduce the base profile.

In particular, during start-up of the papermaking machine, the operator will select the proper base profile from the database. The zeta potential apparatus continuously develops zeta potential profiles which are compared to the base zeta potential profile. The chemical addition is adjusted until the measured profile matches the base profile. Continual monitoring of the measured zeta potential profile allows the operator to adjust the rate of chemical addition should the measured profile deviated beyond a preset range from base profile. Only the wet end of the machine needs to operate during this initial start-up stage. Materials are recycled during this period.

Specifically, during the initial stage of operation, zeta potential apparatus 86 measures the zeta potential and transmit signals to computer 99 which continuously develops zeta potential profiles. These measured water weight profiles are compared to the base or optimal zeta potential profile that has been selected for the particular grade of paper being made from a database. Referring to FIG. 5, curve A represents a base or optimal profile that has been preselected from the database for the grade of paper that is being made. During the start-up phase, zeta potential measurements at the wire are made by the zeta potential apparatus and, from these measurements, curve B is created using standard curve fitting methods.

As is apparent, as shown in FIG. 5, in this example the measured zeta potential values are higher than those of the base profile. As a result, the computer will transmit appropriate signals to controller 80 that will increase (or decrease) the flow rate of chemical additive through valve 88. This curve comparison procedure continues until the measured zeta potential profile matches the preselected optimized profile. In practice, 100% matching will not be necessary or practical and the level of deviation can be set by the operator. Therefore, it is understood that the term "match" or "matching" implies that the measured zeta potential profile has the same or approximately the same values as that of the preselected base zeta potential profile. Referring to FIG. 5, another method of comparing the measured zeta potential values with those of the base profile entails comparing the five measurements of the five detectors for each profile rather than comparing the two curves. Furthermore, depending on the grade of paper, it may be that measurements at detector 1 may be more significant that those of the other detectors. In this case, the operator may require a higher degree of agreement for detector 1 than for the other ones. After the proper chemical addition rate is reached, i.e., when the measured profile matches the base profile, the dry end process goes on line and finished product is made.

The zeta potential sensors 74 and/or 76 can be similarly employed to control the rate of flow the chemical additives.

STRUCTURE OF THE ELECTRODES IN INDIVIDUAL DETECTORS OF ZETA POTENTIAL APPARATUS

The following describes a preferred detector or sensor of the zeta potential apparatus. FIG. 3 shows a conductivity or resistance measurement system, described in U.S. patent application Ser. No. 08/766,864 which is incorporated herein by reference, which measures the conductivity or resistance of the water in the stock material. The conductivity of the water is proportional to the water weight. A sensor array includes two elongated grounded electrodes 24A and 24B and a segmented electrode 24C. Measurement cells (cell1, cell2, ... celln) each include a segment of electrode 24C and a corresponding portion of the grounded electrodes (24A and 24B) opposite the segment. Each cell detects the conductivity of the paper stock and specifically the water portion of the stock residing in the space between the segment and its corresponding opposing portions of grounded electrode.

Although the sensor array may comprise multiple cells, it is understood that each detector of the zeta potential required only one cell structure, e.g., cell 2 of FIG. 3. Indeed, even though the preferred detector comprises three electrodes, two of which are grounded, the required number of electrodes is only two, with one being ground.

Each cell is independently coupled to an input voltage (Vin) from signal generator 25 through an impedance element Zfixed and each provides an output voltage to voltage detector 26 on bus Vout. Signal generator 25 provides Vin.

Device 26 includes circuitry for detecting variations in voltage from each of the segments in electrodes 24C and any conversion circuitry for converting the voltage variations into useful information relating to the physical characteristics of the aqueous mixture. Optional feedback circuit 27 includes a reference cell having similarly configured electrodes as a single cell within the sensor array. The reference cell functions to respond to unwanted physical characteristic changes in the aqueous mixture other than the physical characteristic of the aqueous mixture that is desired to be measured by the array. For instance, if the sensor is detecting voltage changes due to changes in weight, the reference cell is configured so that the weight remains constant. Consequently, any voltage/conductivity changes exhibited by the reference cell are due to aqueous mixture physical characteristics other than weight changes (such as temperature and chemical composition). The feedback circuit uses the voltage changes generated by the reference cell to generate a feedback signal (Vfeedback) to compensate and adjust Vin for these unwanted aqueous mixture property changes (to be described in further detail below). It should also be noted that the non-weight related aqueous mixture conductivity information provided by the reference cell may also provide useful data in the sheetmaking process.

The sensor array is sensitive to three physical properties of the material being detected: the conductivity or resistance, the dielectric constant, and the proximity of the material to the sensor. Depending on the material, one or more of these properties will dominate. The material capacitance depends on the geometry of the electrodes, the dielectric constant of the material, and its proximity to the sensor. For a pure dielectric material, the resistance of the material is infinite (i.e., $Rm=\infty$) between the electrodes and the sensor measures the dielectric constant of the material. Alternatively, for a highly conductive material, the resistance of the material is much less than the capacitive impedance (i.e., $Rm<<Z_{Cm}$), and the sensor measures the conductivity of the material.

FIG. 4 illustrates an electrical representation of a measuring apparatus including cells 1–n of sensor array 24 for measuring conductivity of an aqueous material. As shown, each cell is coupled to Vin from signal generator 25 through an impedance element which, in this embodiment, is resistive element Ro. Referring to cell n, resistor Ro is coupled to center segment 24D(n) and portions 24A(n) and 24B(n) (opposite segment 24D(n)) are coupled to ground. Also shown in FIG. 6 are resistors Rs1 and Rs2 which represent the conductance of the aqueous mixture between the segments and the grounded portions. Resistors Ro, Rs1, and Rs2 form a voltage divider network between Vin and ground.

The measuring apparatus shown in FIG. 4 is based on the concept that the conductivity of the voltage divider network Rs1 and Rs2 of the aqueous mixture and the weight/amount of an aqueous mixture are inversely proportional. Consequently, as the weight increases/decreases, the combination of Rs1 and Rs2 decreases/increases. Changes in Rs1 and Rs2 cause corresponding fluctuations in the voltage Vout as dictated by the voltage divider network. The voltage Vout from each cell is coupled to detector 26. Hence, variations in voltage inversely proportional to variations in conductivity of the aqueous mixture are detected by detector 26 thereby providing information relating to the weight and amount of aqueous mixture in the general proximity above each cell. Detector 26 also typically includes other circuitry for converting the output signals from the cell into information representing particular characteristics of the aqueous mixture.

FIG. 4 also shows feedback circuit 27 including reference cell 28 and feedback signal generator 29. The concept of the feedback circuit 27 is to isolate a reference cell such that it is affected by aqueous mixture physical characteristic changes other than the physical characteristic that is desired to be sensed by the system. For instance, if weight is desired to be sensed then the weight is kept constant so that any voltage changes generated by the reference cell are due to physical characteristics other than weight changes. In one embodiment, reference cell 28 is immersed in an aqueous mixture of recycled water which has the same chemical and temperature characteristics of the water in which sensor array 24 is immersed in. Hence, any chemical or temperature changes affecting conductivity experienced by array 24 is also sensed by reference cell 28. Furthermore, reference cell 28 is configured such that the weight of the water is held constant. As a result voltage changes Vout(ref. cell) generated by the reference cell 28 are due to changes in the conductivity of the aqueous mixture, caused from characteristic changes other than weight. Feedback signal generator 29 converts the undesirable voltage changes produced from the reference cell into a feedback signal that either increases or decreases Vin and thereby cancels out the affect of erroneous voltage changes on the sensing system. For instance, if the conductivity of the aqueous mixture in the array increases due to a temperature increase, then Vout(ref. cell) will decrease causing a corresponding increase in the feedback signal. Increasing Vfeedback increases Vin which, in turn, compensates for the initial increase in conductivity of the aqueous mixture due to the temperature change. As a result, Vout from the cells only change when the weight of the aqueous mixture changes.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An apparatus, for measuring an electrical characteristic of an aqueous fibrous composition comprising fibers dispersed in an aqueous phase, comprising at least three detectors, designated $d_1$, $d_2$, $d_3$, and so on, that are sensitive to properties of the fibrous composition and which are positioned in tandem wherein each detector comprises:

(a) an impedance element; and
   (b) a sensor including a first electrode and a second electrode which is spaced-apart and adjacent to said first electrode, a portion of said aqueous fibrous composition being between and in close proximity to said first and said second electrodes, said sensor coupled in series with said impedance element between an input signal and a reference, wherein fluctuations in at least one of the properties characteristic cause changes in voltage across said sensor, wherein each detector comprises a housing having an inlet and outlet and defining a channel through which said aqueous fibrous composition travels, wherein the outlet of a first conductivity detector $d_1$ is in communication with the inlet of a second conductivity detector $d_2$, the outlet of $d_2$ is in communication with the inlet of a third conductivity detector $d_3$, and so on, and wherein the channels of said at least three detectors have different configurations.

2. The apparatus of claim 1 wherein the channel of $d_1$ has a cross sectional area that is larger than that of $d_2$, the channel of $d_2$ has a cross sectional area that is larger than that of $d_3$, and so on.

3. The apparatus of claim 1 wherein each detector has a channel with a rectangular cross section, and wherein the height for each channel is different.

4. The apparatus of claim 1 wherein for at least one of said detectors, the first electrode is coupled to the impedance element and said second electrode is coupled to the reference potential.

5. The apparatus of claim 4 wherein for each of said detectors, the first electrode is coupled to the impedance element and said second electrode is coupled to the reference potential, wherein each of said detectors includes a third electrode that is coupled to the reference potential, the first electrode being spaced-apart and residing between the second and the third electrodes, and wherein another portion of the material is between and in close proximity to the first and the third electrodes.

6. The apparatus of claim 1 wherein for at least one of said detectors, the first electrode is coupled to said input signal and the second electrode is coupled to the impedance element.

7. The apparatus of claim 1 wherein for at least one of said detectors further includes a third electrode coupled to the reference potential, the first electrode being spaced-apart and residing between the second and the third electrodes, wherein another portion of the material is between and in close proximity to the first and the third electrodes.

8. The apparatus of claim 1 wherein said apparatus further comprises a means for providing a feedback signal to adjust said input signal such that said fluctuations in at least one of said properties are due to fluctuations in a single physical characteristic of said material.

9. The apparatus of claim 8 wherein said physical properties include conductivity, and proximity of said portion of said material to said sensor and said single physical characteristic of said material comprises one of material weight, chemical composition, and temperature.

10. The apparatus of claim 1 wherein the fluctuations in the conductivity cause changes in voltage across said sensor.

11. The apparatus of claim 1 wherein the reference potential is ground.

* * * * *